(12) United States Patent
Prisner et al.

(10) Patent No.: US 8,570,033 B2
(45) Date of Patent: Oct. 29, 2013

(54) DOUBLE-RESONANCE STRUCTURE AND METHOD FOR INVESTIGATING SAMPLES BY DNP AND/OR ENDOR

(75) Inventors: Thomas Prisner, Bad Vilbel (DE); Vasyl Denysenkov, Frankfurt am Main (DE)

(73) Assignee: Johann Wolfgang Goethe-Universität Frankfurt am Main, Frankfurt am Main (DE)

( * ) Notice: Subject to any disclaimer, the term of this patent is extended or adjusted under 35 U.S.C. 154(b) by 448 days.

(21) Appl. No.: 12/936,069

(22) PCT Filed: Apr. 3, 2009

(86) PCT No.: PCT/EP2009/002488
§ 371 (c)(1),
(2), (4) Date: Nov. 15, 2010

(87) PCT Pub. No.: WO2009/121630
PCT Pub. Date: Oct. 8, 2009

(65) Prior Publication Data
US 2011/0050225 A1    Mar. 3, 2011

(30) Foreign Application Priority Data
Apr. 3, 2008 (DE) .......................... 10 2008 017 135

(51) Int. Cl.
*G01R 33/34* (2006.01)
(52) U.S. Cl.
USPC ............................. 324/307; 324/309; 324/318
(58) Field of Classification Search
USPC ................................................ 324/307, 318
See application file for complete search history.

(56) References Cited

FOREIGN PATENT DOCUMENTS

JP    2005-121409    5/2005

OTHER PUBLICATIONS

Avdievich, Nikolai; "Multifrequency Probe for Pulsed EPR and ENDOR Spectroscopy"; Nov. 7, 2001; Journal of Magnetic Resonance, vol. 153, pp. 178-185.*
Weis, et al, "High-Field DNP and ENDOR with a Novel Multiple-Frequency Resonance Structure", *Journal of Magnetic Resonance*, vol. 140, pp. 293-299, Sep. 1999.
Burghaus, et al., "A novel high-field/high-frequency EPR and ENDOR spectrometer operating at 3 mm wavelength", *Measurement Science and Technology*, vol. 3, No. 8, pp. 765-774, Aug. 1, 1992.
Singel, et al., "A Spectrometer for EPR, DNP, and Multinuclear High-Resolution NMR", *Journal of Magnetic Resonance*, vol. 81, pp. 145-161, Jan. 1, 1989.

(Continued)

*Primary Examiner* — Melissa Koval
*Assistant Examiner* — Rishi Patel
(74) *Attorney, Agent, or Firm* — Sunstein Kann Murphy & Timbers LLP

(57) ABSTRACT

A double-resonance structure for DNP-NMR experiments and/or ENDOR experiments and methods using such a double-resonance structure. The double-resonance structure comprises a microwave resonator for generating electromagnetic fields suitable for EPR and an HF resonator for generating electromagnetic fields suitable for NMR. The HF resonator is formed by a strip resonator, a section of the strip resonator at the same time forming a portion of the microwave resonator.

29 Claims, 4 Drawing Sheets

(56) References Cited

OTHER PUBLICATIONS

Sloop, et al., "Spin-Echo-ENDOR Studies of the Photoexcited Triplet State of Pentacene in p-Terphenyl Crystals at Room Temperature", *Journal of Magnetic Resonance*, vol. 86, pp. 156-159, Jan. 1, 1990.

Johansson, et al., "A stripline resonator for ESR", *Review of Scientific Instruments USA*, vol. 45, No. 11, pp. 1445-1447, Nov. 1974.

International Searching Authority, International Preliminary Report on Patentability and Written Opinion of International Searching Authority, Mar. 4, 2009.

International Searching Authority, English translation of International Preliminary Report on Patentability and Written Opinion of International Searching Authority, Mar. 4, 2009.

* cited by examiner

US 8,570,033 B2

DOUBLE-RESONANCE STRUCTURE AND METHOD FOR INVESTIGATING SAMPLES BY DNP AND/OR ENDOR

The present application is a US National Phase application based on PCT/EP2009/002488, and, like the latter application, claims priority from German application Serial No. 10 2008 017 135.2, filed Apr. 3, 2008, which is incorporated herein by reference.

BACKGROUND OF THE INVENTION

The present invention relates to a double-resonance structure for DNP experiments and/or ENDOR experiments. Furthermore, it relates to a method for investigating samples by DNP and/or ENDOR.

Nuclear magnetic resonance spectroscopy (NMR spectroscopy) is one of the most important spectrographic methods for elucidating the structure and dynamics of molecules, in particular in organic chemistry and biochemistry. However, the sensitivity of NMR spectrometers reaches its limits in many applications, for example, in investigation of large biomolecules in vitro and in vivo. The lack of sensitivity can be improved to a certain extent by applying a stronger external magnetic field, but this is possible only to a limited extent and at a very high cost.

A very promising alternative for increasing the sensitivity of NMR measurements in biomolecules, for example, consists of a method known as "dynamic nuclear polarization" or "DNP method" from the abbreviation of the English term "dynamic nuclear polarization." DNP results from the transfer of spin polarization from electrons to nuclei according to the principle known as the "Overhauser effect." To make DNP usable in NMR spectroscopy, the electron spin polarizations must first be transferred to the nuclear spin system. To do so, the sample is excited at an electron spin resonance frequency, usually referred to as the EPR frequency, where EPR is the abbreviation for the English term "electronic paramagnetic resonance." The EPR frequency, also known as the Larmor frequency, corresponds to the splitting of energy of electron spin energy quantum states of an atom or molecule in an external magnetic field according to the Zeeman effect, which would be degenerate in the absence of an external magnetic field. The splitting of the energy states is proportional to the strength B of the external magnetic field, and thus the value of the EPR frequency is a function of the magnetic field strength. However, the EPR frequency is always in the microwave range in applications of practical relevance. The change in polarization of the electron spin due to input of EPR microwaves is often referred graphically to as "pumping".

The amplification of the NMR signals due to DNP is proportional to the square of the intensity of the EPR microwave field as long as the EPR transitions are not saturated. Microwave resonators in which the sample is arranged for stimulation of the EPR transitions are preferably used to obtain an EPR microwave field with the highest possible power and/or field strength.

As in EPR, nuclear magnetic resonance (NMR) is also based on transitions between quantum states of a spin in an external magnetic field, except that the energy splitting of the nuclear spins is much smaller than in EPR. NMR frequencies are typically in a two-digit megahertz range, i.e., still in the high-frequency (HF) range. The literature also uses the term "radio frequency" instead of the term "high frequency". However, the term "high frequency" should not make us forget that these NMR frequencies are actually the lower frequencies of the system, namely lower than the aforementioned microwave frequencies. Since a high intensity of the HF field is also necessary for NMR spectroscopy, an HF resonance coil is also preferably used. So-called double-resonance structures, which have a microwave resonator for EPR transitions and an HF coil for NMR transitions, are therefore advantageous, so that the same sample may be arranged at the same time in a MW field and in an HF field with high intensities.

So-called "electron nuclear double-resonance spectroscopy" or ENDOR spectroscopy is a method related to DNP-NMR spectroscopy in terms of its conception. ENDOR spectroscopy is a special type of EPR spectroscopy, in which NMR transitions in a sample are induced by applying HF fields. To this extent, ENDOR spectroscopy is conceptually very similar to DNP-NMR spectroscopy, except that in this case pumping is performed in HF fields, and EPR spectroscopy is performed. A double-resonance structure is also used for ENDOR experiments.

A double-resonance structure is known from the article by Weis et al. (High-field DNP and ENDOR with novel multiple-frequency resonance structure, J. Magn. Reson. 140, 293-299 (1999)). This previously known double-resonance structure comprises a cylindrical microwave resonator formed from a helically coiled conductive strip. The helically coiled conductive strip forms a coil which assumes the function of the HF resonator. The cylindrical MW resonator is therefore also referred to as the helix resonator. An iris is formed in the lateral surface of the helix through which microwaves can be fed to the helix resonator. The length of the resonator may be adjusted by adjustable pistons inserted into the helix at both ends.

In the known helix resonator, a cylindrical $TE_{011}$ microwave mode can be excited so that a very high microwave energy density can be achieved in the MW resonator. However, the dimensions of the helix resonator correlate with the wavelength, and if the wavelength of the microwaves drops below a millimeter in strong magnetic fields according to the EPR conditions, the small size of the helix resonator limits the sample volume that can be accommodated in the helix resonator.

In the case of liquid samples, in particular aqueous samples, there is also the problem in using the known helix resonator that far less than its entire volume can be used for accommodating the sample volume because the sample would heat up too much from the application of microwaves. The reason for the strong heating is the frequency-dependant dielectric permittivity of water under the influence of microwaves. For example, the complex dielectric permittivity of water at a microwave frequency of 260 GHz has a real part $\in'=5.6$ and an imaginary part $\in''=5.8$, where the dielectric losses are proportional to the imaginary part $\in''$ of the permittivity. The relatively strong losses, also known as "insertion losses", result in the fact that, on the one hand, the MW field in the sample is considerably weaker than the field outside of the sample, and on the other hand, the sample is heated strongly.

For example, if biomolecules in aqueous solutions are to be investigated, high heating of the sample is out of the question because the biomolecules might be destroyed by heating. The present inventors used an aqueous sample in a capillary with a diameter of only 0.1 mm on a trial basis and found that the temperature of the sample was raised by 90° C. under the influence of microwaves. Even at a capillary diameter of only 0.05 mm, there was still a heating of 17° C. This means that the sample volume must always be kept relatively small, so that the filling factor $$\eta = \frac{V_s \langle B_{HF}^2 \rangle_s}{V_{struk} \langle B_{HF}^2 \rangle_{struk}}$$

is relatively small here, leading to a reduced NMR sensitivity. Herein, $V_s$ is the volume of the sample, $\langle B^2_{HF} \rangle$ is the average value of the magnetic field strength $\langle B^2_{HF} \rangle_s$ in the area of the sample, $V_{struk}$ is the volume of the structure and $\langle B^2_{HF} \rangle_{struk}$ is the average value of the magnetic field strength $B_{HF}$ of the field in the area of the structure. If the MW power is reduced to prevent excessive heating of the sample, this leads to a weakening of the DNP and thus in turn to a negative effect on the NMR sensitivity.

Another double-resonance structure, a so-called cavity resonator for ENDOR is described in JP2005-121409. The resonator has an HF coil wound around the sample, which is in turn arranged in an MW cavity. This structure is suitable for ENDOR spectroscopy but not for DNP applications because the HF coil leads to a disturbance in the distribution of the electrical MW field over the sample volume, which leads to disadvantageous heating of the sample.

The object of the present invention is to provide a double-resonance structure and a method for investigating specimens by means of DNP-NMR and/or ENDOR, which will allow an increased measurement sensitivity.

BRIEF SUMMARY OF EMBODIMENTS OF THE INVENTION

This object is achieved by a double-resonance structure and a method. The method is characterized by the use of the inventive double-resonance structure. Advantageous further embodiments are defined in the dependent claims.

The double-resonance structure according to the present invention differs from that known from the state of the art in that the HF resonator is formed by a strip resonator, where a section of the strip resonator at the same time forms a part of the MW resonator.

The "strip resonator" may be formed by any strip conductor that is a suitable resonator for the HF field and at the same time can be used as part of the MW resonator. One example of such a strip resonator may be a "stripline resonator" or a "microstrip resonator". By using such a strip resonator, HF fields for NMR transitions can be generated with sufficient strength. At the same time, the strip resonator forms a section of the MW resonator. The MW frequencies that are relevant here are so-called quasi-optical microwaves, and said section of the strip resonator may form a reflector for an MW resonator. At the MW frequencies that are relevant here, said section of the strip resonator or stripline resonator serves as a reflector of the MW resonator on which the microwaves are more or less optically reflected. This creates a more open structure in comparison with the helix resonator and this structure is advantageous with regard to the dissipation of heat, allowing the use of larger sample volume than is possible with the known helix resonator.

In an advantageous further embodiment, the MW resonator comprises a spherical reflector and a planar reflector for microwaves positioned opposite one another such that the planar reflector is formed by a section of the strip resonator. Such an MW resonator is also known as a "semiconfocal Fabry-Perot resonator". In this arrangement, the strip resonator thus has a triple function:

Firstly, it generates an HF field whose magnetic field strength $B_{HF}$ is greater than that of the known helix resonator. This corresponds to an increased NMR sensitivity.

Secondly, the strip resonator serves as a reflector in the MW resonator, so that the different resonators can be combined ideally without mutually interfering with one another in their function. The resulting structure offers sufficient space for sample volumes, which may be larger by a factor of 10 than those with the known helix resonator.

And thirdly, the strip resonator acts as a heat sink, which dissipates the heat generated especially when an aqueous sample is irradiated with microwaves, so that even relatively large volumes of sample can be used without excessive heating.

An iris through which microwaves can be fed into the MW resonator is preferably formed in the spherical reflector. Furthermore, the spherical reflector and the planar reflector are preferably designed and arranged in such a way that a microwave magnetic field can develop in the $TEM_{00n}$ mode of the MW resonator. Use of the $TEM_{00n}$ mode allows high magnetic field strengths to be generated in a comparatively large volume range, so that comparatively large sample volumes can in turn be investigated.

The strip resonator preferably has a first end, which is connected to ground potential, and the section of the strip resonator forming a part of the MW resonator is arranged in the area of the first end of the strip resonator. At the grounded end of the strip resonator, the voltage reaches a minimum and therefore the current is at a maximum, so that the magnetic field $B_{HF}$ generated in the strip resonator is at its maximum in the area of the grounded end. This arrangement thus results in HF magnetic fields $B_{HF}$ being at their maximum in the area of the MW resonator, where the sample is situated, which leads to an increased NMR sensitivity.

The strip resonator preferably has a second end, in which a capacitor for adjusting the resonant frequency of the strip resonator is provided.

In an especially advantageous embodiment of the double-resonance structure, a place is provided for holding the sample, this location being connected to the strip resonator in a thermally conducting manner. For example, the place for holding the sample may be designed so that the sample held there is in direct contact with the strip resonator. Therefore, heat generated by absorption of microwaves in the sample can be dissipated efficiently by the strip resonator. This design is ideally suited for spectroscopic investigation of aqueous samples, which may be allowed to heat only slightly, in particular for investigation of biomolecules in aqueous solution.

A connection for an HF line, for example, for a coaxial cable over which the HF signals can be applied to the strip resonator, is preferably provided. The term "signals" is to be understood broadly and includes any type of electromagnetic waves, pulses, stimulating pulses, etc. An adjustable matching capacitor is preferably provided between the strip resonator and the connection for HF signals, over which the coupling of signals into the strip resonator can be optimized.

In an advantageous embodiment, the double-resonance structure is designed as a probe and/or a specimen head, which can be inserted into a borehole in a magnet. This magnet, into which the specimen head can be inserted, is intended for generating a static magnetic field, in which the essentially degenerate quantum states of the specimen are split through interaction of the electron spin and/or nuclear spin with the external static magnet field. The specimen head preferably has a housing connected to ground potential. The strip resonator together with this grounded housing then forms a so-called stripline structure.

In a preferred embodiment, the strip resonator is formed by an elongated section of a conductor surface, which is separated by nonconducting omissions from the remainder of the conductor surface along a portion of its length. As explained in greater detail below on the basis of an exemplary embodiment, a concentration of the HF magnetic field near the sample can be achieved through this design because the magnetic field lines run through the nonconductive recesses, and the magnetic field is thus concentrated in the area of the strip resonator section of the surface. The conductive surface may be a metallization layer, for example, which is formed on a dielectric substrate. The nonconductive omissions may be formed by regions in which the metallization is omitted. However, a similar effect may also be achieved by a slotted conductive plate.

The double-resonance structure described here can be further embodied to form a DNP-NMR spectrometer. To do so, a microwave conductor, which is connected to the double-resonance structure for input of microwaves into the MW resonator, and an NMR device are provided and are connected to the double-resonance structure for input of HF signals into the strip resonator and for receiving HF signals from the strip resonator.

Likewise, the inventive double-resonance structure may be further embodied to an ENDOR spectrometer, in which a microwave source, which is connected to the double-resonance structure for supplying microwaves into the MW resonator and for receiving MW signals from the MW resonator, and an HF source, which is connected to the double-resonance structure for supplying HF signals into the strip resonator, are provided. Furthermore, the inventive double-resonance structure may be used in a combined DNP-NMR/ENDOR spectrometer, which is capable of both modes of operation.

BRIEF DESCRIPTION OF FIGURES

Additional advantages and features of the devices and the method according to the present invention are derived from the following description, in which the invention is explained in greater detail on the basis of an exemplary embodiment with reference to the accompanying drawings, in which.

DETAILED DESCRIPTION OF PREFERRED EMBODIMENTS

Figure 1:
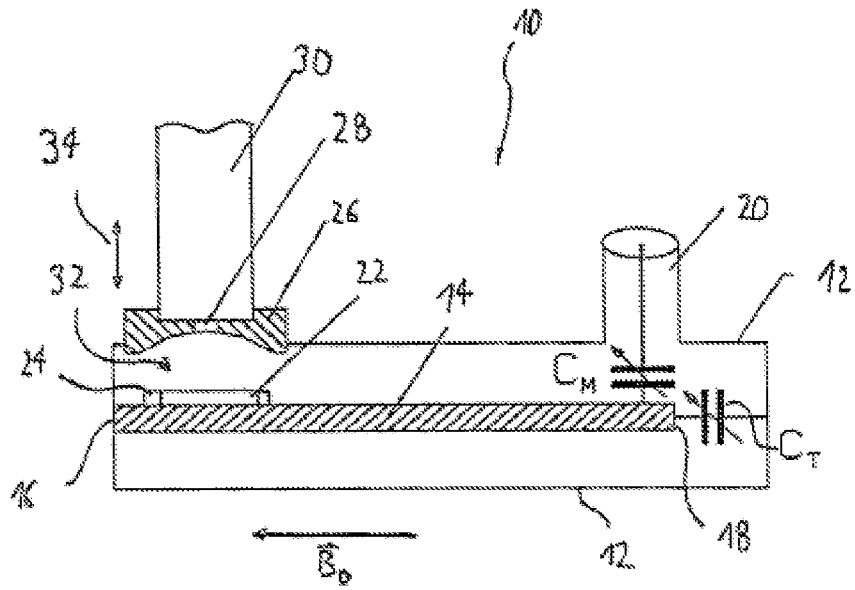
FIG. 1 shows a longitudinal sectional view of the resonance structure according to an embodiment of the invention.
Figure 2:
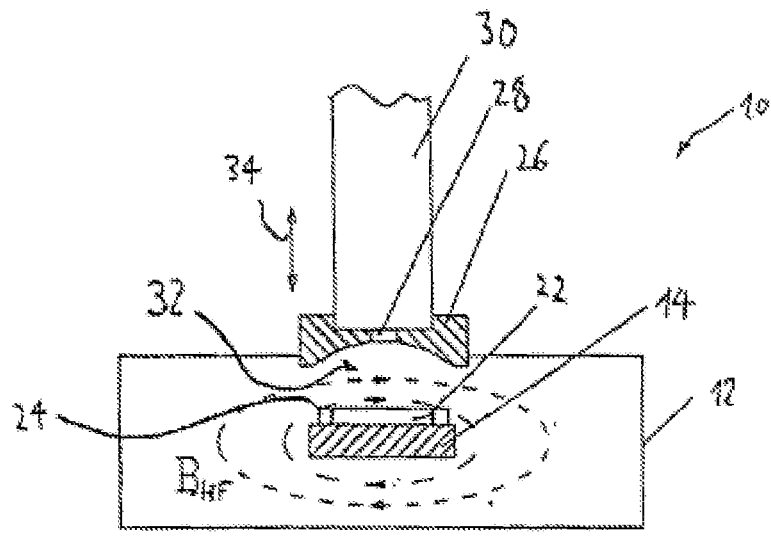
FIG. 2 shows a cross-sectional view of the double-resonance structure of FIG. 1, showing magnetic field lines $B_{HF}$ of the HF field.
Figure 3:
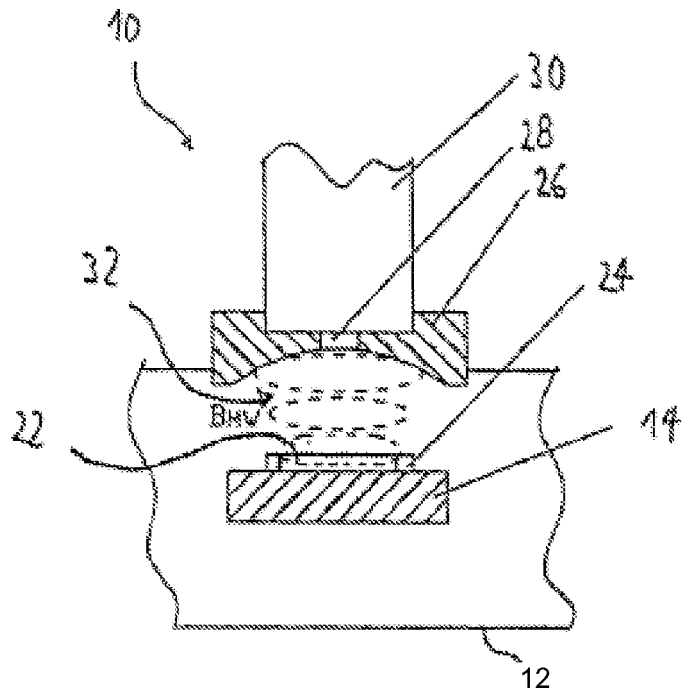
FIG. 3 shows a cross-sectional view of the double-resonance structure of FIG. 1, showing magnetic field lines $B_{MW}$ of the microwave field.

FIG. 1 shows a double-resonance structure 10 in a longitudinal sectional view, and FIGS. 2 and 3 show the same double-resonance structure 10, each in a cross-sectional view. The double-resonance structure 10 comprises a housing 12, which is connected to ground potential. A strip resonator 14 is arranged in the housing 12. The strip resonator 14 is a strip-shaped internal conductor, which is connected at its left end 16 in FIG. 1 to the housing 12, so that the first end 16 is also at ground potential. Such a strip resonator is also known as a "stripline" or "microstrip". The strip resonator 14 has a second end 18, which is at the right in the representation of FIG. 1. An adjustable capacitor $C_T$ is arranged between the second end 18 and the housing 12. By adjusting the capacitance of the capacitor $C_T$, the resonant frequency of the strip resonator 14 can be adjusted.

In the area of the second end 18 of the strip resonator 14, a connection 20 for an HF line (not shown), for example a coaxial cable, is provided. HF signals from an HF source can be applied to the strip resonator 14 via this connection and optionally also received by the strip resonator 14. To be able to optimize the coupling between these HF signals and the strip resonator 14, a capacitor CM whose capacitance is also adjustable is connected between the connection 20 and the second end of the strip resonator 14. Such a capacitor is also known as a "matching capacitor".

A sample 22 is arranged near the first end 16 of the strip resonator 14. The sample 22 may be an aqueous sample, for example, containing the biomolecules to be investigated. The sample 22 is inside a small Teflon ring, which is placed on the strip resonator. The sample 22 is filled into the interior of the ring 24 and is thus arranged directly on the surface of the strip resonator 14. The volume of the sample 22 may be 200 mL, for example.

A spherical reflector 26 in which an iris 28 is formed is situated above the sample 22. The spherical reflector 26 is connected to a waveguide 30 for microwaves by means of which microwaves can be fed into the interspace between the strip resonator 14 and the spherical reflector 26. The iris 28 may be slotted to generate linearly polarized microwave modes or may be circular to generate circularly polarized microwave modes.

The spherical reflector 26 and the section of the strip resonator 14 opposite the spherical reflector 26 form a microwave resonator 32, which is also referred to as a semiconfocal Fabry-Perot resonator. The distance between the spherical reflector 26 of the MW resonator 32 and the strip resonator 14 is adjustable, as indicated schematically by the double arrow 34. The resonant frequency of the MW resonator 32 can be adjusted by varying the distance between the spherical reflector 26 and the strip resonator 14.

The function of the double-resonance structure 10 of FIG. 1 is described below:

The term "double resonance" indicates that resonance conditions for two different electromagnetic fields are created in the area of sample 22. One resonance pertains to the resonance of strip resonator 14, which is operated at a frequency corresponding to an NMR resonance in an external magnetic field $B_0$. At an external magnetic field $B_0$ of approximately 10 T, the NMR frequency amounts to approximately 400 MHz, for example. The field line of the high-frequency magnetic field $B_{HF}$ generated by the resonator 14 is diagramed schematically in FIG. 2. Since the resonator is connected to ground potential at its first end 16, the currents and thus the magnetic field $B_{HF}$ are at their maximum at this first end 16. The sample 22 is arranged in this maximum magnetic field $B_{HF}$.

The second resonance of the double-resonance structure relates to a resonance in the microwave range, namely at frequencies which correspond to EPR transitions. At an external magnetic field $B_0$ of approximately 10 T, the EPR resonant frequency is approximately 260 GHz. The corresponding microwave field is formed in the resonator 32, and the magnetic field $B_{MW}$ of this mode is diagramed schematically in FIG. 3. The mode formed in the MW resonator 32 is referred to as the $TEM_{00n}$ mode, where n is an integer. The mode $TEM_{00n}$, is axially symmetrical, and the field profile in a plane parallel to the surface of the strip resonator 14 has a Gaussian shape with a width which depends on the distance from the spherical reflector 26. The highest magnetic field strength of the MW magnetic field is $B_{MW}$, which occurs directly at the surface of the strip resonator 14, i.e., where the sample 22 is arranged. The next peak of the magnetic field strength $B_{MW}$ is located one-half of a wavelength above the surface of strip resonator 14. Therefore, the maximum thickness of the sample 22 is preferably approximately 10% of the resonant wavelength. If the sample 22 were thicker, it would also be in the range of the standing wave with a high electric field, so that the sample material 22 would be excessively heated and the quality factor Q of the resonator 32 would be impaired.

Since the sample 22 is arranged directly on the strip resonator 14, heat can be dissipated from the sample by the resonator in this way. This is an advantage in particular in comparison with a helix resonator, for example, with which heating is difficult to prevent because of microwave absorption, except with very small sample volumes and a low microwave power, which would in turn reduce the measurement accuracy.

By utilizing the double-resonance, DNP-NMR experiments or ENDOR experiments can be performed. In DNP-NMR experiments, electron spins in the sample 22 are polarized by the microwave field and this polarization is transferred to the nuclear spins according to the Overhauser effect, resulting in an elevated NMR signal in measurement of NMR spectra. In ENDOR experiments, the reverse case occurs: The sample is excited with NMR frequencies and EPR spectra are measured. The double-resonance structure 10 is suitable for both types of experiments and may thus be used as a probe or sample head for both an ENDOR spectrometer and a DNP-NMR spectrometer. It can also be used in a combined ENDOR/DNP-NMR spectrometer, optionally operated in both of these two modes, with a suitable microwave bridge connected to the microwave waveguide 30 and a suitable NMR device connected to the HF connection 20.

Figure 5:
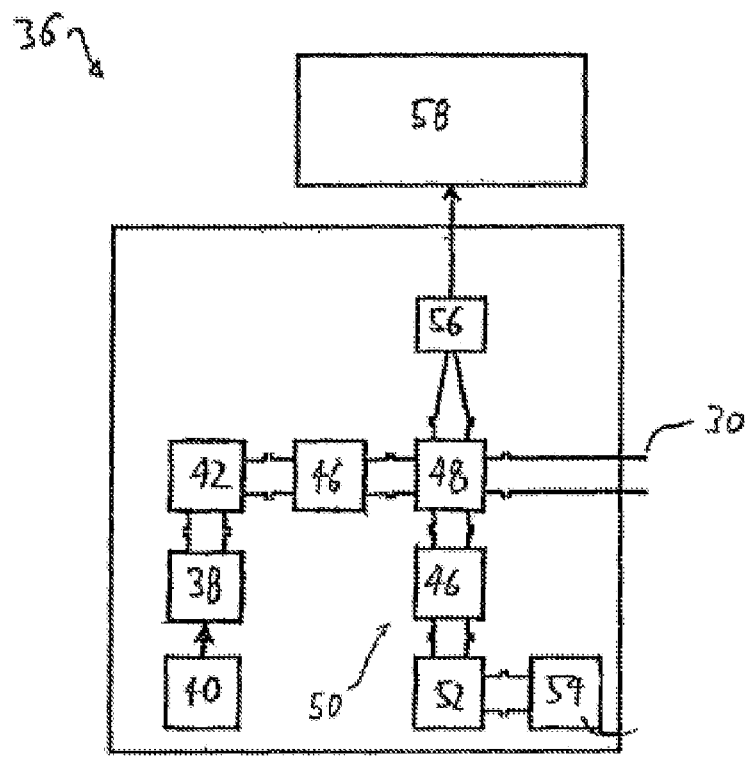
FIG. 5 shows a schematic diagram of the components of a microwave bridge.
Figure 6:
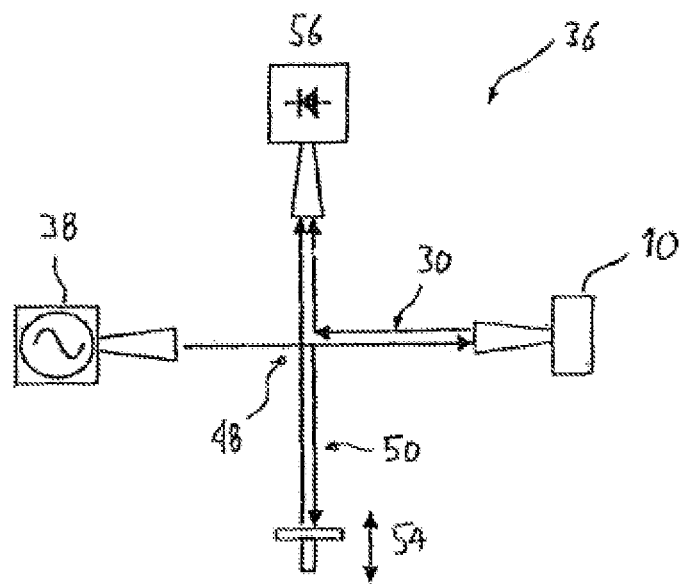
FIG. 6 shows a functional diagram of the microwave bridge of FIG. 5.

An example of a suitable microwave bridge 36 is shown in FIGS. 5 and 6. FIG. 5 shows the essential components of the microwave bridge 36 in a block diagram, and FIG. 6 shows the functional design of the microwave bridge 36.

As shown in FIG. 5, the microwave bridge 36 comprises a microwave oscillator 38, which is connected to a voltage supply 40. Furthermore, the microwave bridge 36 comprises a detector 56 which is connected to a lock-in amplifier 58. The corresponding components are labeled with the same reference numerals as in FIG. 6.

The microwave bridge 36 of FIGS. 5 and 6 may be operated in an EPR detection mode and in a DNP mode. To do so, the microwave bridge 36 is designed as a Michelson interferometer, as shown especially well in FIG. 6, where the EPR spectroscopy is performed with the help of a signal of the microwaves reflected by the microwave resonator 32. The highest EPR sensitivity can be achieved when the beam splitter 48 directs half of the incident power into the reference arm 50 and into the signal arm, i.e., the microwave waveguide 30. The splitting of the power is not optimal for the DNP mode, however, because in the DNP mode as much microwave power as possible should be fed into the double-resonance structure, i.e., into the signal arm. To this end, the beam splitter 48 may be replaced by an alternative beam splitter, which allows 99.5% of the power to pass into the signal arm (waveguide 30), for example, and deflects only 0.5% of the power into the reference arm 50.

In the DNP-NMR mode, the HF connection 20 of the double-resonance structure 10 is connected to a traditional NMR device, a so-called NMR console. In the ENDOR mode, the HF connection 20 is connected to a suitable HF source instead of to the NMR console.

Figure 4:
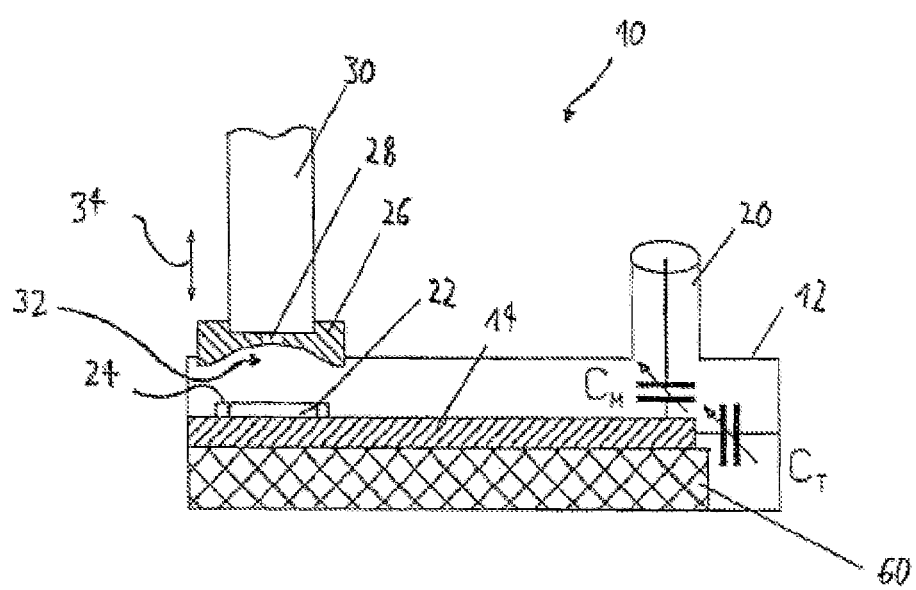
FIG. 4 shows a longitudinal section illustrating an alternative embodiment of a double-resonance structure.

FIG. 4 shows an alternative embodiment of the double-resonance structure 10, in which the strip resonator 14 is arranged on a dielectric substrate 60. A strip resonator 14 arranged on such a substrate 60 is also referred to as a "microstrip".

Figure 7:
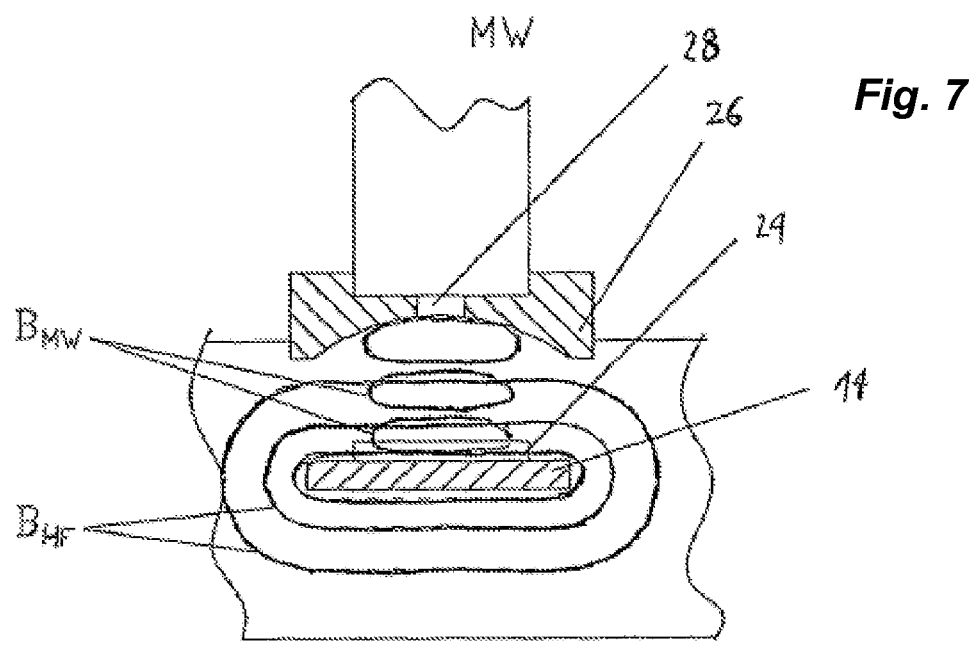
FIG. 7 shows a cross-sectional view of a double-resonance structure like that of FIGS. 2 and 3, in which the magnetic field lines $B_{MW}$ of the microwave field and the magnetic field lines $B_{HF}$ of the HF field are illustrated.
Figure 8:
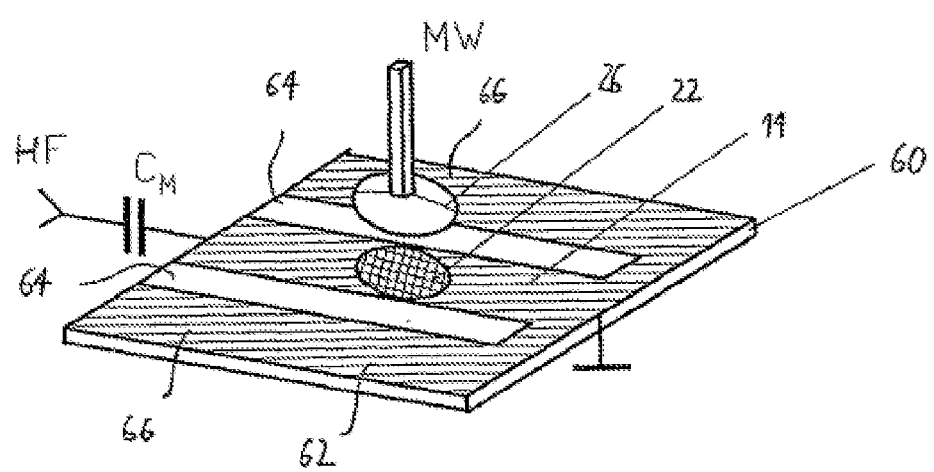
FIG. 8 shows a schematic perspective view illustrating an alternative embodiment of a double-resonance structure.

FIG. 7 shows a cross-sectional view like that in FIG. 2 and FIG. 3, which show the microwave magnetic field $B_{MW}$ as well as the HF magnetic field $B_{HF}$. In the embodiments in FIGS. 1 to 4, the HF field $B_{HF}$ is enclosed in the housing 12. The housing 12 thus helps to localize the magnetic field. FIG. 8 shows an alternative embodiment with which the magnetic field $B_{HF}$ can be concentrated in the vicinity of the sample 22 in a particularly advantageous manner and in which no housing is required. In the embodiment of FIG. 8, like that of FIG. 4, a dielectric layer 60 is provided, and a metallization layer 62, represented by hatching in FIG. 8, is arranged thereon. Two elongated omissions 64 in the metallization layer are provided on both sides of the sample 22, so that the metallized layer 62 is subdivided into three strip-shaped sections: a central section 14, which forms the strip resonator, and two outer sections 66. When a high-frequency alternating electric field is applied to the left end of the middle section 14 in the diagram in FIG. 8, i.e., the "strip resonator 14", a corresponding magnetic field $B_{HF}$ (not shown in FIG. 8) is induced, surrounding the central section 14 as shown in FIG. 7 and passing through the bare strip 64. Therefore, the HF field $B_{HF}$ is concentrated near the sample 22 so that a strong magnetic field can develop at the site of the sample. At the same time, this design has the advantage that it concentrates the HF field even without a housing, which promotes the dissipation of heat. Furthermore, the exterior strips 66 also support the dissipation of heat without interfering with the spatial concentration of the magnetic field.

As shown in the above exemplary embodiments, the double-resonance structure 10 of the present invention allows DNP-NMR and ENDOR experiments with very strong NMR and EPR fields and comparatively large sample volumes. In fact, the sample volumes that can be used are approximately ten times larger than those possible with the helix resonator known from the state of the art and described in the introduction here. One particular advantage of the double-resonance structure 10 is that it is able to dissipate heat from the sample very effectively, so that biomolecules in aqueous solution, for example, can be investigated despite the high absorbed microwave power without a rise in temperature of the sample to an unacceptable extent. This makes the double-resonance structure 10 extremely advantageous for investigating liquid and/or aqueous samples in particular.

The double-resonance structure shown here is suitable in particular for structural analysis of biomolecules (2D-NMR), kinetic studies (because the measurement times are greatly reduced), analysis of complex (bio)molecule mixtures, for example, analysis of metabolites, identification and monitoring of impurities and for ligand and biomarker screening. Furthermore, dynamic molecular interactions can be investigated in an advantageous manner with the double-resonance structure 10. In addition, the double-resonance structure can be used in 2D and 3D analyses of condensed material, for example, ordered crystals, lipid layers and membranes and for NMR microscopy.

In an ENDOR spectroscopy mode, the double-resonance structure can be used advantageously in investigating defects in semiconductors, chiralities and endohedral complexes (fullerenes).

Although various exemplary embodiments of the invention have been disclosed, it should be apparent to those skilled in the art that various changes and modifications can be made which will achieve some of the advantages of the invention without departing from the true scope of the invention.

LIST OF REFERENCE NUMERALS

10 Double-resonance structure
12 Housing
14 Strip resonator
16 First end of strip resonator 14
18 Second end of strip resonator 14
20 HF connection
22 Sample
24 Sample ring
26 Spherical reflector
28 Iris
30 Waveguide
32 MW resonator
34 Double arrow
36 Microwave bridge
38 MW oscillator
40 Voltage source
42 Mechanical microwave switch
46 Attenuator
48 Beam splitter
50 Reference arm
52 Wave measurement device
54 Reflector
56 Detector
58 Lock-in amplifier
60 Dielectric substrate
62 Metallization layer
64 Bare strip in the metallization layer 62
66 External metallization strip

What is claimed is:

1. A double-resonance structure for DNP-NMR and/or ENDOR experiments, the double resonance structure comprising:
a microwave resonator, including at least one planar reflector, for generating electromagnetic fields suitable for EPR; and
an HF resonator for generating electromagnetic fields suitable for NMR, formed by a strip resonator, such that a section of the strip resonator at the same time forms the planar reflector of the microwave resonator.

2. The double-resonance structure according to claim 1, wherein the microwave resonator additionally includes a spherical reflector for microwaves which is opposite from the planar reflector.

3. The double-resonance structure according to claim 2, wherein an iris is formed in the spherical reflector through which the microwaves can be supplied into the microwave resonator.

4. The double-resonance structure according to claim 3, wherein the iris is slot-shaped to generate linearly polarized microwave modes in the microwave resonator.

5. The double-resonance structure according to claim 3, wherein the iris is circular to generate circularly polarized microwave modes in the microwave resonator.

6. The double-resonance structure according to claim 2, wherein the spherical reflector and the planar reflector are designed and arranged, so that a $TEM_{00n}$ microwave mode can be formed between them.

7. The double-resonance structure according to claim 1, wherein the microwave resonator is connected to a microwave source and can be operated in the lowest radiation mode of the microwave resonator.

8. The double-resonance structure according to claim 1, wherein the strip resonator has a first end, which is at ground potential, and a section of the strip resonator forming part of the microwave resonator is arranged in the area of the first end of the strip resonator.

9. The double-resonance structure according to claim 8, wherein the strip resonator has a second end on which a capacitor $C_T$ is provided for adjusting the resonant frequency of the strip resonator.

10. The double-resonance structure according to claim 1, wherein a place having a thermally conducting connection to the strip resonator is provided for holding a sample.

11. The double-resonance structure according to claim 9, wherein the place for holding a sample is designed so that the sample being held is in direct contact with the strip resonator.

12. The double-resonance structure according to claim 10, wherein the place for holding the sample includes a device for holding a liquid sample.

13. The double-resonance structure according to claim 12, wherein the level of the liquid sample to be held amounts one-tenth or less of the resonant wavelength of the microwave resonator.

14. The double-resonance structure according to claim 1, wherein a connection for an HF line, by means of which the HF signals can be applied to the strip resonator, is provided.

15. The double-resonance structure according to claim 14, wherein an adjustable matching capacitor $C_M$ is provided between the strip resonator and the connection for HF signals.

16. The double-resonance structure according to claim 1, which is designed as a sample head insertable into a borehole in a magnet.

17. The double-resonance structure according to claim 16, wherein the sample head has a housing, which is connected to ground potential.

18. The double-resonance structure according to claim 1, wherein the strip resonator is formed by a section of a conductor surface, which is separated from the remainder of the conductor surface along a portion of its length by nonconductive omissions.

19. The double-resonance structure according to claim 18, wherein the conductor surface is formed by a metallization layer on a dielectric substrate, and the nonconductive omissions are formed by areas where the metallization is omitted.

20. A double-resonance structure for DNP and/or ENDOR experiments, comprising a microwave resonator with a conductive spherical reflector and an iris, by means of which the spherical reflector is coupled to a microwave source or a microwave receiver, and with a conductive planar strip-shaped reflector, which at the same time functions as an HF resonator.

21. A DNP-NMR spectrometer, comprising the following: a double-resonance structure, said double-resonance structure having a microwave resonator for generating electromagnetic fields suitable for EPR, and having an HF resonator for generating electromagnetic fields suitable for NMR, wherein the HF resonator is formed by a strip resonator such that a section of the strip resonator at the same time forms a planar reflector of the microwave resonator,
 a microwave source connected to the double-resonance structure for input of microwaves into the microwave resonator, and an NMR device connected to the double-resonance structure for input of HF signals into the strip resonator and for receiving HF signals from the strip resonator.

22. An ENDOR spectrometer comprising:
 a double-resonance structure, said double-resonance structure having a microwave resonator for generating electromagnetic fields suitable for EPR, and having an HF resonator for generating electromagnetic fields suitable for NMR, wherein the HF resonator is formed by a strip resonator such that a section of the strip resonator at the same time forms a planar reflector part of the microwave resonator;
 a microwave source connected to the double-resonance structure for input of microwaves into the microwave resonator and for receiving microwaves from the microwave resonator; and
 an HF source connected to the double-resonance structure for input of HF signals into the strip resonator.

23. A combined DNP-NMR/ENDOR spectrometer comprising:
 a double-resonance structure, said double-resonance structure having a microwave resonator for generating electromagnetic fields suitable for EPR, and having an HF resonator for generating electromagnetic fields suitable for NMR, wherein the HF resonator is formed by a strip resonator such that a section of the strip resonator at the same time forms a planar reflector of the microwave resonator;
 a microwave device suitable for input of microwave signals into the microwave resonator of the double-resonance structure in an NMR mode, and for input of microwaves into the microwave resonator of the double-resonance structure and for receiving and detecting microwave signals from the microwave resonator in an ENDOR mode; and
 a high-frequency device suitable for input of HF signals into the strip resonator of the double-resonance structure, receiving and detecting HF signals from the strip resonator in an NMR mode, and for input of HF signals into the strip resonator in an ENDOR mode.

24. A method for investigating samples by means of DNP-NMR and/or ENDOR, the method comprising:
 arranging a sample in a double-resonance structure, said double-resonance structure comprising a microwave resonator and an HF strip resonator wherein the HF strip resonator forms a planar reflector of the microwave resonator;
 generating a microwave field, said microwave field being suitable for inducing EPR transitions in the sample; and
 generating an HF field, said HF field being suitable for inducing NMR transitions in the sample, the method characterized in that the HF resonator is formed by a strip resonator, such that a section of the strip resonator at the same time forms a part of the microwave resonator.

25. The method according to claim 24, wherein the microwave resonator comprises a spherical reflector and a planar reflector for microwaves, which are opposite one another, such that the planar reflector is formed by a section of the strip resonator.

26. The method according to claim 25, wherein an iris, through which microwaves are fed into the microwave resonator, is formed in the spherical reflector.

27. The method according to claim 24, wherein a $TEM_{00n}$ mode is generated in the microwave resonator.

28. The method according to claim 24, wherein the sample is liquid.

29. The method according to claim 24, wherein the sample is in thermally conducting contact with the strip resonator, in particular being applied directly to the strip resonator.

* * * * *

UNITED STATES PATENT AND TRADEMARK OFFICE
CERTIFICATE OF CORRECTION

PATENT NO. : 8,570,033 B2  
APPLICATION NO. : 12/936069  
DATED : October 29, 2013  
INVENTOR(S) : Prisner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 490 days.

Signed and Sealed this

Twenty-second Day of September, 2015

Michelle K. Lee  
*Director of the United States Patent and Trademark Office*